(12) United States Patent
Mona et al.

(10) Patent No.: US 10,351,498 B2
(45) Date of Patent: *Jul. 16, 2019

(54) PROCESS FOR GENERATING HEMP OIL WITH A HIGH CANNABIDIOL (CBD) CONTENT

(71) Applicant: CV SCIENCES, INC., San Diego, CA (US)

(72) Inventors: Michael J. Mona, San Diego, CA (US); Joshua A. Hartsel, San Diego, CA (US); Greg Waterbury, San Diego, CA (US)

(73) Assignee: CV SCIENCES, INC., San Diego, CA (US)

(*) Notice: Subject to any disclaimer, the term of this patent is extended or adjusted under 35 U.S.C. 154(b) by 271 days.

This patent is subject to a terminal disclaimer.

(21) Appl. No.: 15/141,553

(22) Filed: Apr. 28, 2016

(65) Prior Publication Data

US 2017/0022132 A1    Jan. 26, 2017

Related U.S. Application Data

(63) Continuation of application No. 14/791,184, filed on Jul. 2, 2015, now Pat. No. 9,340,475.

(60) Provisional application No. 62/020,053, filed on Jul. 2, 2014.

(51) Int. Cl.
| | | |
|---|---|---|
| *B01D 3/10* | (2006.01) |
| *B01D 3/14* | (2006.01) |
| *C11B 3/00* | (2006.01) |
| *C11B 3/12* | (2006.01) |
| *B65D 73/00* | (2006.01) |
| *B65D 75/36* | (2006.01) |
| *C07C 37/50* | (2006.01) |
| *C07C 37/70* | (2006.01) |
| *C07C 37/74* | (2006.01) |
| *C07D 311/80* | (2006.01) |

(52) U.S. Cl.
CPC .............. *C07C 37/50* (2013.01); *B01D 3/106* (2013.01); *B01D 3/148* (2013.01); *C07C 37/70* (2013.01); *C07C 37/74* (2013.01); *C07D 311/80* (2013.01); *C11B 3/00* (2013.01); *C11B 3/001* (2013.01); *C11B 3/12* (2013.01); *B65D 73/0092* (2013.01); *B65D 75/367* (2013.01); *C07C 2601/16* (2017.05)

(58) Field of Classification Search
CPC ............ B01D 3/106; C11B 3/00; C07C 37/50
USPC ....................................................... 568/805
See application file for complete search history.

(56) References Cited

U.S. PATENT DOCUMENTS

| | | | |
|---|---|---|---|
| 6,403,126 B1 | 6/2002 | Webster et al. | |
| 8,980,941 B2 | 3/2015 | Hospodor | |
| 9,340,475 B2 * | 5/2016 | Mona, III | ................. C11B 3/00 |
| 2004/0033280 A1 | 2/2004 | Whittle | |

(Continued)

OTHER PUBLICATIONS

International Search Report and Written Opinion for PCT/US2015/039140 (12 pages).

*Primary Examiner* — Deborah D Carr
(74) *Attorney, Agent, or Firm* — Procopio, Cory, Hargreaves & Savitch LLP

(57) ABSTRACT

A method for producing hemp oil, comprising decarboxylation of CBDA in hemp oil; short-path evaporation of CBD from the decarboxylated hemp oil to produce CBD oil; selective THC to CBN conversion performed on the decarboxylated hemp oil.

7 Claims, 4 Drawing Sheets

(56) References Cited

U.S. PATENT DOCUMENTS

2004/0049059 A1    3/2004   Mueller
2006/0167283 A1    7/2006   Flockhart et al.
2010/0168448 A1    7/2010   Flockhart et al.
2012/0046352 A1    2/2012   Hospodor

* cited by examiner

CBD - cannabidiol

CBN - cannabinol

THC - delta 9 tetrahydrocannabinol

PROCESS FOR GENERATING HEMP OIL WITH A HIGH CANNABIDIOL (CBD) CONTENT

CROSS-REFERENCE TO RELATED APPLICATIONS

This application claims the benefit of application Ser. No. 14/791,184 filed on Jul. 2, 2015, which claims the benefit under provisional application No. 62/020,053, filed on Jul. 2, 2014, and the contents of the aforementioned application are incorporated herein by reference in their entirety.

BACKGROUND

Field of the Invention

The embodiments described herein are related to generating hemp oil, and more particularly to an improved process that generates hemp oil with a high CBD content.

Related Art

Cannabinoids are a class of diverse chemical compounds that act on cannabinoid receptors on cells that modulate physiological responses in the brain, peripheral nervous and immune systems. The native endocannabinoid ligands (produced naturally in the body by humans and animals), the phytocannabinoids (found in cannabis and some other plants), and synthetic cannabinoids (manufactured chemically) bind to receptors throughout the body and control downstream signal transduction. One example of a cannabinoid is Cannabidiol (CBD), which is a major substituent in hemp and hemp extracts. The chemical compound for CBD is illustrated in FIG. 5. Some researchers believe that CBD shows promise of potential clinical applications in a variety of medical conditions. It may have multiple potential applications such as for the treatment of epilepsy and other motor disorders, inflammation, mood and anxiety disorders, sleep dysfunction and eating disorders. CBD is also considered a promising antineoplastic agent on the basis of its in vitro and in vivo activity against tumor cells.

The endocannabinoid system (ECS) regulates many physiological processes involved in relaxation, eating, sleeping, certain inflammatory responses and even cognitive function. There are two types of cannabinoid receptors found throughout the body (CB1 and CB2), but they are most abundant in the brain and immune system respectively. In fact, the CB1 receptor is the most densely populated G-coupled protein receptor in the human brain. New evidence indicates that a cannabinoid-like ligands act on wide variety of biological targets, such as the transient receptor potential cation channel, nuclear receptors and other orphaned G-coupled protein receptors (i.e., TRPV1, PPAR, GPR18 and GPR55), and represents a fascinating area to develop new therapeutic targets.

CB1 receptors are found primarily in the brain, more specifically in the basal ganglia and in the limbic system, including the hippocampus. They are also found in the cerebellum and in both male and female reproductive systems. CB1 receptors are absent in the medulla oblongata, the part of the brain stem responsible for respiratory and cardiovascular functions. Thus, there is not the risk of respiratory or cardiovascular failure that can be produced by some drugs, such as opioids. CB1 receptors appear to be responsible for the euphoric and anticonvulsive effects of cannabis.

CB2 receptors are predominantly found in the immune system or immune-derived cells with the greatest density in the spleen. While found only in the peripheral nervous system, a report does indicate that CB2 is expressed by a subpopulation of microglia in the human cerebellum. CB2 receptors appear to be responsible for the anti-inflammatory and possibly other therapeutic effects of cannabinoids. CBD binds only weakly to both the CB1 and CB2 receptor sites and its health benefits cannot be explained with traditional cannabinoid receptor binding. It is unclear how CBD functions and its mechanism of action is a current topic of investigation.

In order to harness the benefits of CBD, processes have been developed to extract the CBD in hemp oil made from the hemp plant. The percentage of CBD in the hemp oil is therefore an important metric.

SUMMARY

The embodiments described herein illustrate a process for producing hemp oil with a high CBD content.

A method for producing hemp oil, comprising decarboxylation of CBDA in hemp oil; short-path evaporation of CBD from the decarboxylated hemp oil to produce CBD oil; selective THC to CBN conversion performed on the decarboxylated hemp oil.

These and other features, aspects, and embodiments are described below in the section entitled "Detailed Description."

BRIEF DESCRIPTION OF THE DRAWINGS

Features, aspects, and embodiments are described in conjunction with the attached drawings, in which.

DETAILED DESCRIPTION

Figure 4:
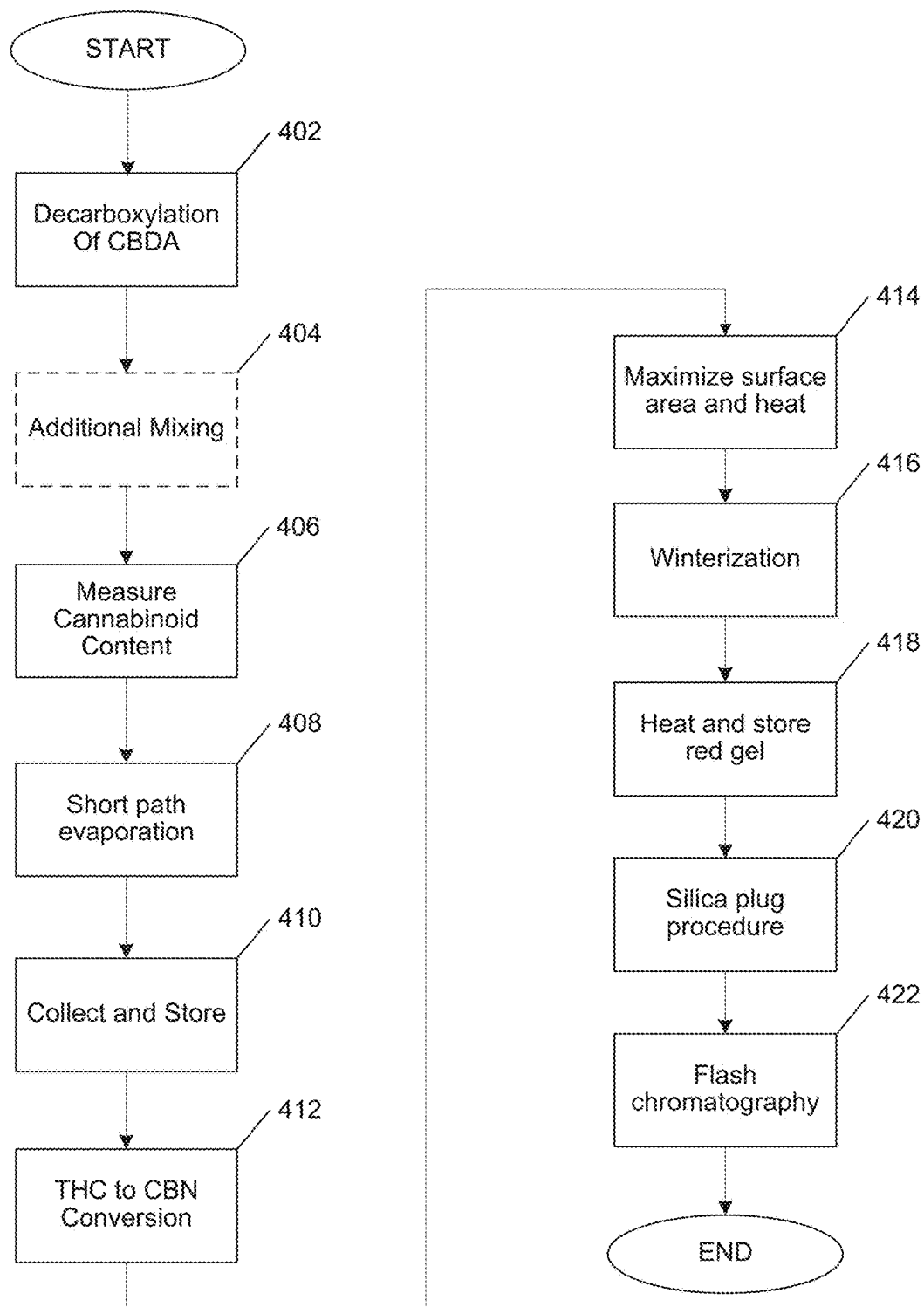
FIG. 4 is a flow chart illustrating and example process for producing hemp oil with a high CBD content in accordance with one embodiment.

Various steps for producing hemp oil are described below. It will be understood that certain steps described can be optional and that the order of the steps may vary. FIG. 4 is a flow chart illustrating an example process for producing hemp oil with a high CBD content in accordance with one example embodiment.

The process can start, in step 402, with Decarboxylation of cannabidiolic acid (CBDA) in Hemp Oil, which can start with virgin CO2 extracted hemp oil that has been extracted from the whole plant. The virgin C02 extracted hemp oil generally has large amounts of cannabidiolic acid (CBDA), the precursor to cannabidiol (CBD). The virgin hemp oil can be decarboxylated by heating to about 150° C., e.g., to a temperature in the range of 140° C. to 160° C. between 10-18 hours, to convert the CBDA to CBD. This procedure can be carried out in a feed tank equipped with a heat transfer oil filled jacket and a venting port to prevent pressure from building up in the vessel.

Upon reaching the decarboxylation temperature, carbon dioxide begins to vigorously boil out of the solution. The bubbling may provide sufficient mixing and will typically subside as the process nears completion; however, if required, additional mixing can be performed using an agitator, in optional step 404. The temperature can then be lowered to between 75-90° C. and the melted contents can then be poured into food grade vessels that can then be stored in a cool dry environment.

At this point, in step 406, cannabinoid content should be measured to ensure full decarboxylation has taken place. If not, then the process should be repeated until full decarboxylation has taken place (<0.1% CBDA).

Next, in step 408, short-path evaporation of CBD from decarboxylated hemp oil can be performed. In this step, CBD can be isolated from the crude decarboxylated CO2 extract using two tandem short-path evaporation steps. Generally, up to 60% (w/w) CBD is obtained using the optimized conditions depending on the input feed material CBD concentration. 30-200 kg of decarboxylated hemp oil can be placed in the feed tank of a, e.g., model KD10 (ChemTech Services) short-path evaporator. The feed tank heat transfer oil bath can be set at 90-150° C. and the solid allowed to fully melt. A vacuum range of 0.5-0.08 torr for evaporator #1 should then be maintained with, e.g., two vacuum pumps (D65B and WAU251). Evaporator #2 was equipped with an Edwards EO50/60 Diffusion Pump capable of achieving an ultimate vacuum of approximately 0.005 torr. The wiper baskets can be set to, e.g., rotate at about 70% of the maximum speed. Evaporator #1 can be set to a range of 250-270° C., depending on the vacuum at system equilibrium and fed at a rate of 2-3.5 Hz from the feed tank pump. Evaporator #2 temperatures of 160-175° C. are generally found to be optimal. The distillate from evaporator #1 is transferred directly to evaporator #2 at the speed at which it is recovered.

Figure 3:
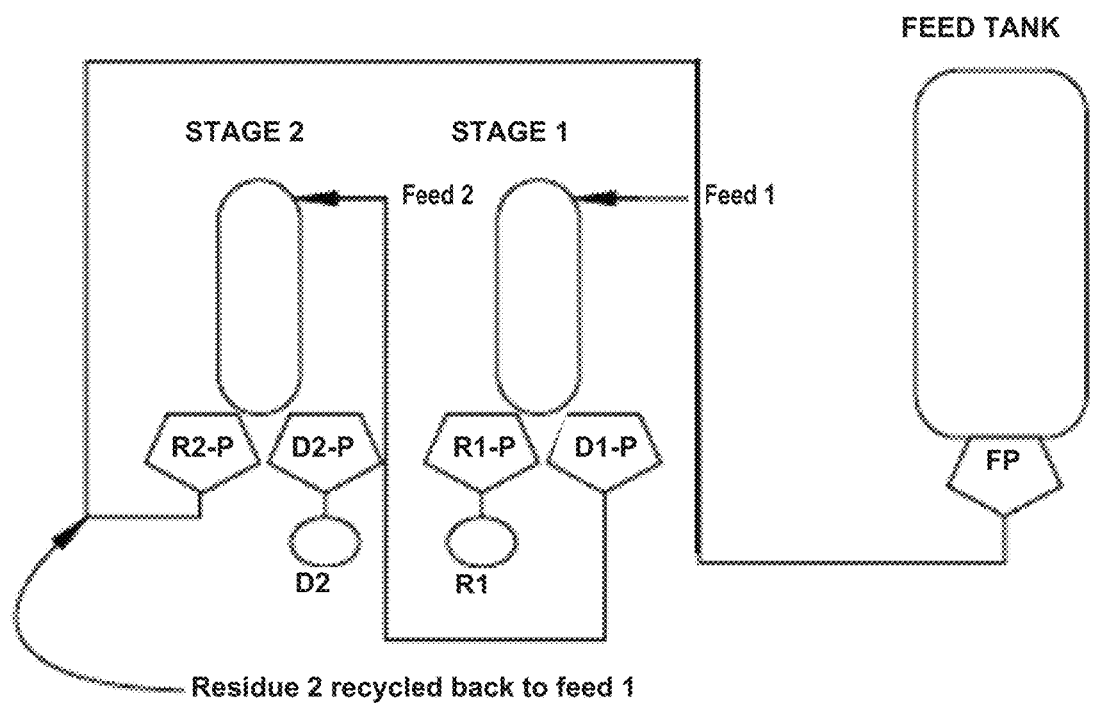
FIG. 3 is an illustration of the 2 stage short path distillation plant that can be used in the process of FIG. 4.

The first step in this sub-process (evaporator #1) is intended to remove as much light boiling volatile components as possible from the CBD-containing feedstock. The second step, of this sub-process, in-series evaporator #2 is used to refine the CBD from the high boiling point components in order to achieve maximum purity. FIG. 3 is an illustration of the 2 stage short path distillation plant.

The distillate can then be collected in food grade vessels and stored in a cool dry environment, in step 410. Cannabinoid content in both the waste residue and distillate should be measured and mass balance determined.

Figure 5:
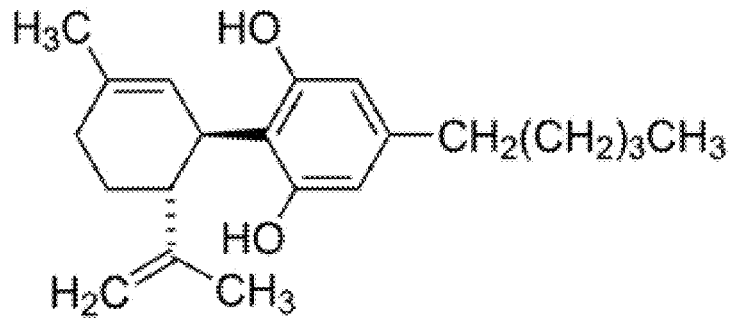
FIG. 5 is a diagram illustrating a CBD compound.
Figure 6:
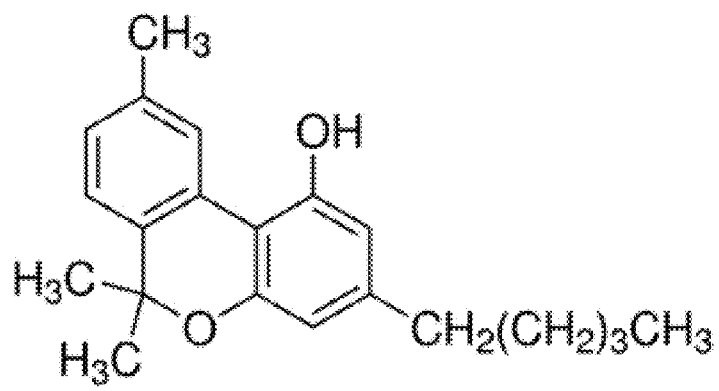
FIG. 6 is a diagram illustrating a CBN compound.
Figure 7:
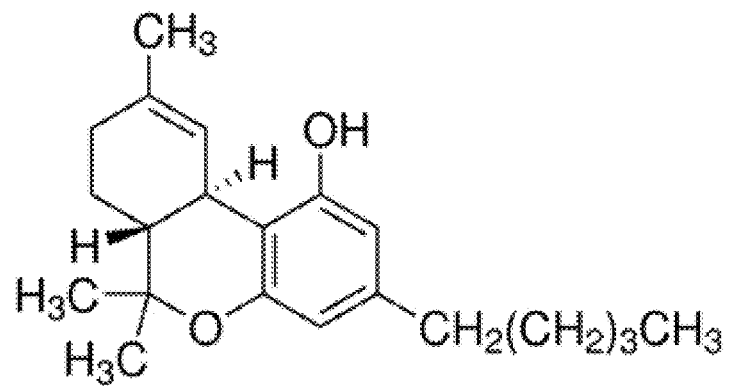
FIG. 7 is a diagram illustrating a THC compound.

The next step (412) can be selective THC to CBN conversion. The purpose of this sub-procedure is to convert residual THC content to cannabinol (CBN) without causing a significant reduction in CBD levels. FIGS. 5 and 6 illustrate example CBN and THC compounds respectively.

The CBD oil purified using short-path evaporation can then, in step 414, be loaded into, e.g., Pyrex baking dish to maximize surface area to atmospheric oxygen and heated from 80-100° C. for a few days to a few weeks. Cannabinoid content is carefully monitored periodically over the conversion period. The hot oil can then be collected in food grade vessels and stored in a cool dry environment.

Figure 1:
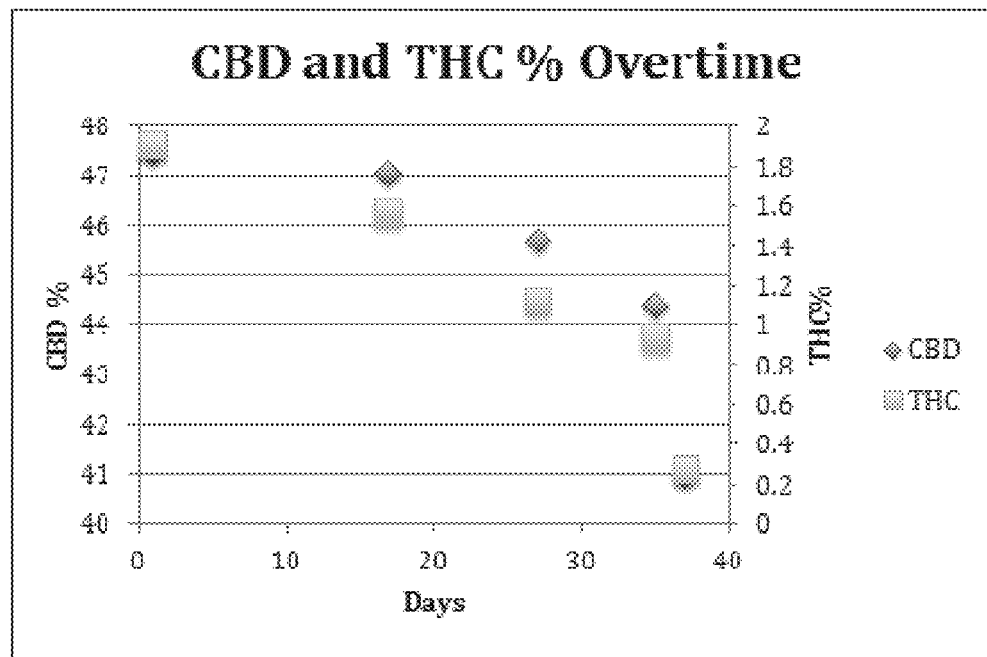
FIG. 1 illustrates the selective thermal degradation (80° C.) of THC content over time in the hemp oil.

Using the process described herein, it has been demonstrated that up to 60% CBD/<1% THC can be obtained starting from material with variable cannabinoid content. FIG. 1 illustrates the selective thermal degradation (80° C.) of CBD and THC percent content over time in the hemp oil. The y-axes represent the THC and CBD percentages, and the x-axis shows days.

Figure 2:
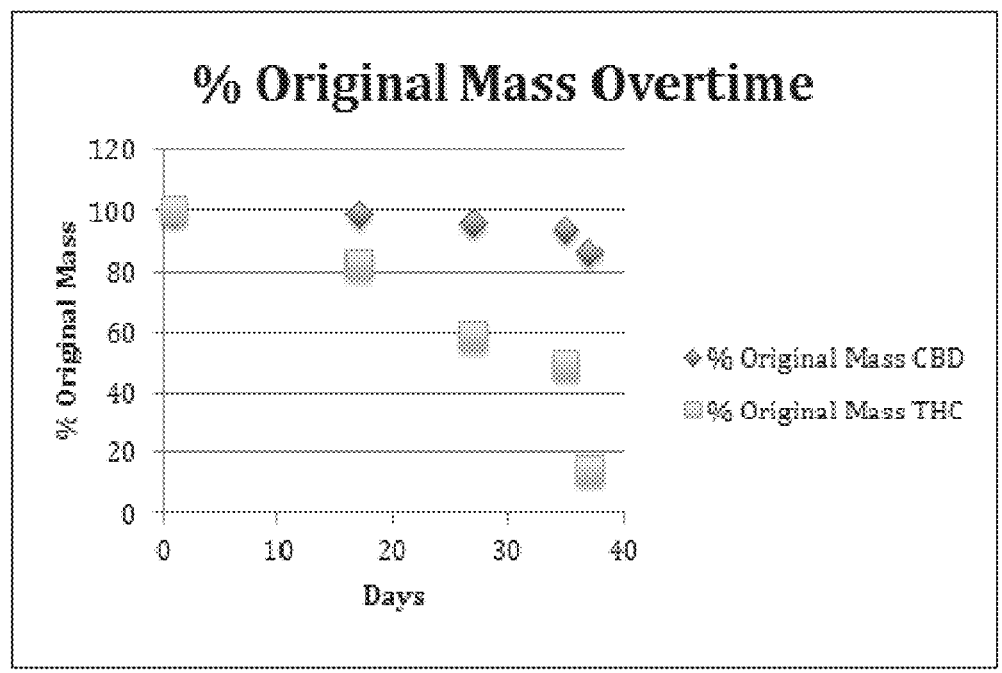
FIG. 2 illustrates the percentage of the original mass overtime during thermal degradation.

FIG. 2 illustrates the percentage of the original mass overtime during thermal degradation. The y-axis represents the percent of each cannabinoid relative to the original percent prior to heating. In addition to minimizing THC content, the procedure described herein decreases the difficulty of isolating pure CBD in future purification steps. Table 1 contains the raw data used to construct the plot.

TABLE 1

| Day | CBD % | % Original Mass CBD | THC % | % Original Mass THC |
| --- | --- | --- | --- | --- |
| 1 | 47.5 | 100 | 1.9 | 100 |
| 17 | 47.05 | 99 | 1.57 | 83 |
| 27 | 45.72 | 96 | 1.12 | 59 |
| 35 | 44.39 | 93 | 0.94 | 49 |
| 37 | 41.01 | 86 | 0.27 | 14 |

Next, a winterization procedure can be performed in step 416. The winterization procedure is designed to remove plant wax impurities from the product. In this procedure the hemp oil is diluted to about 10% (w/w) in isopropanol, placed in a freezer at about −20° C. overnight, and vacuum filtered through a bed of sand at about −20° C. A white solid can then be collected and washed 2× with cold isopropanol. The filtrate can be combined and the solvent stripped under heat in vacuo to produce a red gel.

The red gel can then be brought to about 80° C., in step 418, collected in high-density polypropylene vessels, and stored in a cool dry environment. Cannabinoid content should be measured to determine the purity of the isolate.

Next a silica plug procedure can be performed in step 420. This procedure is performed to remove highly polar impurities that stick to the baseline of normal phase silica gel, which increases purity and reduces overall loading mass in the next process chromatography step. In addition, the silica plug extends the life of the silica gel used during flash chromatography purification. A large glass fritted filter funnel can be charged with silica gel slurry made from, e.g., 95% hexane and 5% ethyl acetate and situated on an Erlenmeyer flask with a sidearm. The winterized CBD-rich oil can then be dissolved in a minimum amount of hexane and loaded onto the top of the column containing a 5:1 silica gel:CBD oil ratio. The product CBD was eluted with a 95% hexane to 5% ethyl acetate solution and collected in fractions. The fractions containing CBD can be combined and the solvent stripped using heat and vacuum to afford a red oil. The red oil can be brought to 80° C. and collected in high-density polypropylene vessels and stored in a cool dry environment. Cannabinoid content should be measured to determine the purity of the isolate.

Next, in step 422, flash chromatography purification of CBD from hemp oil can be performed. The red oil from the silica plug can be diluted in a minimum amount of hexane and loaded on a, e.g., Biotage KP-Sil 1500 g column equilibrated with 93% hexane 7% ethyl acetate with an automated peristaltic pump. This procedure can be carried out on a Biotage Isolera LS using a dual wavelength UV detector (215, 235 nm). An isocratic gradient consisting of about 93% hexane to about 7% ethyl acetate can be maintained throughout the run. The CBD fraction can then be isolated and the solvent removed in vacuo to yield a golden oil. Residual solvent contamination can be removed by placing the oil under high vacuum (0.005 torr) at about 80° C. for about 72 hours. The remaining golden oil can then be transferred to glass vials and stored at about 4° C. Cannabinoid content should be measured to determine the purity of the purified fractions.

While certain embodiments have been described above, it will be understood that the embodiments described are by way of example only. Accordingly, the systems and methods described herein should not be limited based on the described embodiments. Rather, the systems and methods described herein should only be limited in light of the claims that follow when taken in conjunction with the above description and accompanying drawings.

What is claimed:

1. A method for producing hemp oil, comprising:
   decarboxylation of CBDA in hemp oil;
   evaporation of CBD from the decarboxylated hemp oil to produce CBD oil; and
   a selective THC to CBN conversion performed on the decarboxylated hemp oil.

2. The method of claim 1, wherein decarboxylation of CBDA in hemp oil comprises:
   starting with virgin CO2 extracted hemp oil that has been extracted from the whole plant;
   decarboxylating the virgin CO2 extracted hemp oil by heating to 140-160° C. for 10-18 hours to convert the CBDA to CBD.

3. The method of claim 2, wherein upon reaching about 140-160° C., mixing the resultant solution and then lowering the temperature to between about 75-90° C.

4. The method of claim 1, wherein the evaporation of CBD from the decarboxylated hemp oil to produce CBD oil comprises isolating the CBD from a crude decarboxylated CO2 extract generated by decarboxylation of CBDA in hemp oil using two sequential evaporation steps, and wherein the first step comprises:
   placing decarboxylated hemp oil in a feed tank of a first evaporator;
   setting the feed tank heater to between about 90-150° C. and allowing the decarboxylated hemp oil to fully melt;
   maintaining a vacuum of at least 0.5 torr to 0.08 torr with primary vacuum pump.

5. The method of claim 1, wherein the evaporator #1 is set to 250-275° C. with a feed rate of 2-3.5 Hz from a feed tank pump.

6. The method of claim 5, wherein the second step comprises using a second evaporator to refine the CBD to maximum purity.

7. The method of claim 6, wherein the second evaporator is set to 160-175° C. and is equipped with an additional diffusion pump capable of achieving an ultimate vacuum of 0.5-0.005 torr. Evaporator #2 is fed at a rate consistent with the output of the residue from evaporator #1.

* * * * *